United States Patent [19]

Gram

[11] 4,274,290
[45] Jun. 23, 1981

[54] RAPID OPENING, HIGH FLOW CONTROL VALVE FOR HYDRAULIC ACTUATOR

[75] Inventor: Martin M. Gram, Minneapolis, Minn.

[73] Assignee: MTS Systems Corporation, Eden Prairie, Minn.

[21] Appl. No.: 955,807

[22] Filed: Oct. 30, 1978

[51] Int. Cl.³ .................. F15B 21/00; G01N 3/10
[52] U.S. Cl. .............................. 73/837; 91/5; 91/448
[58] Field of Search .............. 73/837; 91/461, 454, 91/445, 5; 251/122, 25, 30; 92/134; 138/45

[56] References Cited

U.S. PATENT DOCUMENTS

| | | | |
|---|---|---|---|
| 2,911,005 | 11/1959 | Adelson | 91/454 X |
| 3,073,349 | 1/1963 | Mitchell | 138/45 |
| 3,084,865 | 4/1963 | Fleer et al. | 251/122 X |
| 3,216,444 | 11/1965 | Herner | 91/443 X |
| 3,228,422 | 1/1966 | Bade | 251/25 X |
| 3,298,389 | 1/1967 | Freeman | 251/122 X |
| 3,407,651 | 10/1968 | Sophy | 73/837 X |
| 3,434,393 | 3/1969 | Cairatti | 91/469 X |
| 3,994,158 | 11/1976 | Weinhold | 73/837 X |
| 4,085,587 | 4/1978 | Garlinghouse | 60/413 X |
| 4,202,174 | 5/1980 | Grigdrenko | 60/413 |

FOREIGN PATENT DOCUMENTS

| | | |
|---|---|---|
| 1807788 | 2/1971 | Fed. Rep. of Germany ............. 92/134 |
| 219448 | 7/1924 | United Kingdom . |
| 244469 | 4/1926 | United Kingdom . |
| 523325 | 7/1940 | United Kingdom . |
| 840690 | 7/1960 | United Kingdom . |
| 989225 | 4/1965 | United Kingdom . |
| 1538128 | 1/1979 | United Kingdom . |

Primary Examiner—Irwin C. Cohen
Attorney, Agent, or Firm—Kinney, Lange, Braddock, Westman and Fairbairn

[57] ABSTRACT

A rapid opening valve assembly utilized in high rate specimen test systems which require that an actuator load a specimen at rates in the range up to one thousand inches per second and with deflections up to three inches. The high rate valve utilizes a poppet or valve piston member that rapidly opens once it is triggered. The ports may be very large and as shown the valve body is used in connection with a closely coupled accumulator pressure source that is ported directly to the actuator to provide adequate flow capacity. The specimen is generally for testing of metals, plastics, and elastomers under tension or compression.

5 Claims, 3 Drawing Figures

RAPID OPENING, HIGH FLOW CONTROL VALVE FOR HYDRAULIC ACTUATOR

BACKGROUND OF THE INVENTION

1. Field of the Invention

The present invention relates to hydraulic control valves, and more particularly to a large capacity rapidly opening valve which provides a high rate of flow for fluid pressure actuators that are to be operated under high velocity and high load.

2. Prior Art

In the past, MTS Systems Corporation of Eden Prairie, Minn., has built what is known as a velocity generator. This is an actuator that provides a relatively high rate of movement. These actuators generally are directly coupled to a pressure source, and have an internal inlet port controlled by a seal on the actuator piston of the velocity generator. The piston is held in position closing the port and when triggered the force holding the piston is reduced and the piston moves slightly and then the entire piston is open to the supply pressure from the built-in accumulator surrounding the velocity generator actuator. Such velocity generators are used for dynamic test systems for impact testing of automotive interiors for example.

Additionally, in the prior art when high velocity actuators were to be used for testing specimens, it has been known to control such actuators with large solenoid valves that will handle up to 400 gallons per minute. Such valves are large, expensive and do not open as quickly as desirable.

SUMMARY OF THE INVENTION

The present invention relates to a fluid pressure control valve which is used in connection with an actuator or hydraulic motor means to provide a quantity of fluid under pressure to the actuator at a sufficiently high rate to permit high rate testing of specimens in tensile and compression loading.

The valve as shown comprises a piston member or poppet that is held in its closed position by a compressible fluid acting on the backside of the valve piston, and when triggered this fluid is reduced in pressure rapidly. The main pressure source for actuating the actuator is acting on a small effective area of the piston, and tends to flow past the valve seat. As soon as the pressure holding the valve piston is reduced sufficiently, i.e., the valve is fired, the operating pressure of the main pressure source acts on a substantial area of the piston and the valve piston fires to full open position. The source of pressure is then open through large passageways directly to the actuator or motor means that is controlled. As shown, a throttle valve is positioned between the valve piston and the actuator which can be used for adjustably controlling the velocity of the controlled actuator to a desired level.

The actuators can be any configuration, but as shown are used for tensile (and also can be used for compression) testing of specimens held by grips in a load frame.

Adequate controls may also be provided to operate the actuator independently of the high rate valve in a normal control configuration. In most instances the actuator must be provided with a cushioning fluid pressure on the side of the actuator piston opposite from that side which receives the actuating pressure.

By making the valve an integral unit with the actuator as shown, the main supply pressure may be an accumulator which provides a known volume of hydraulic oil through ports which are sized to insure adequate flow.

DESCRIPTION OF THE PREFERRED EMBODIMENT

Figure 1:
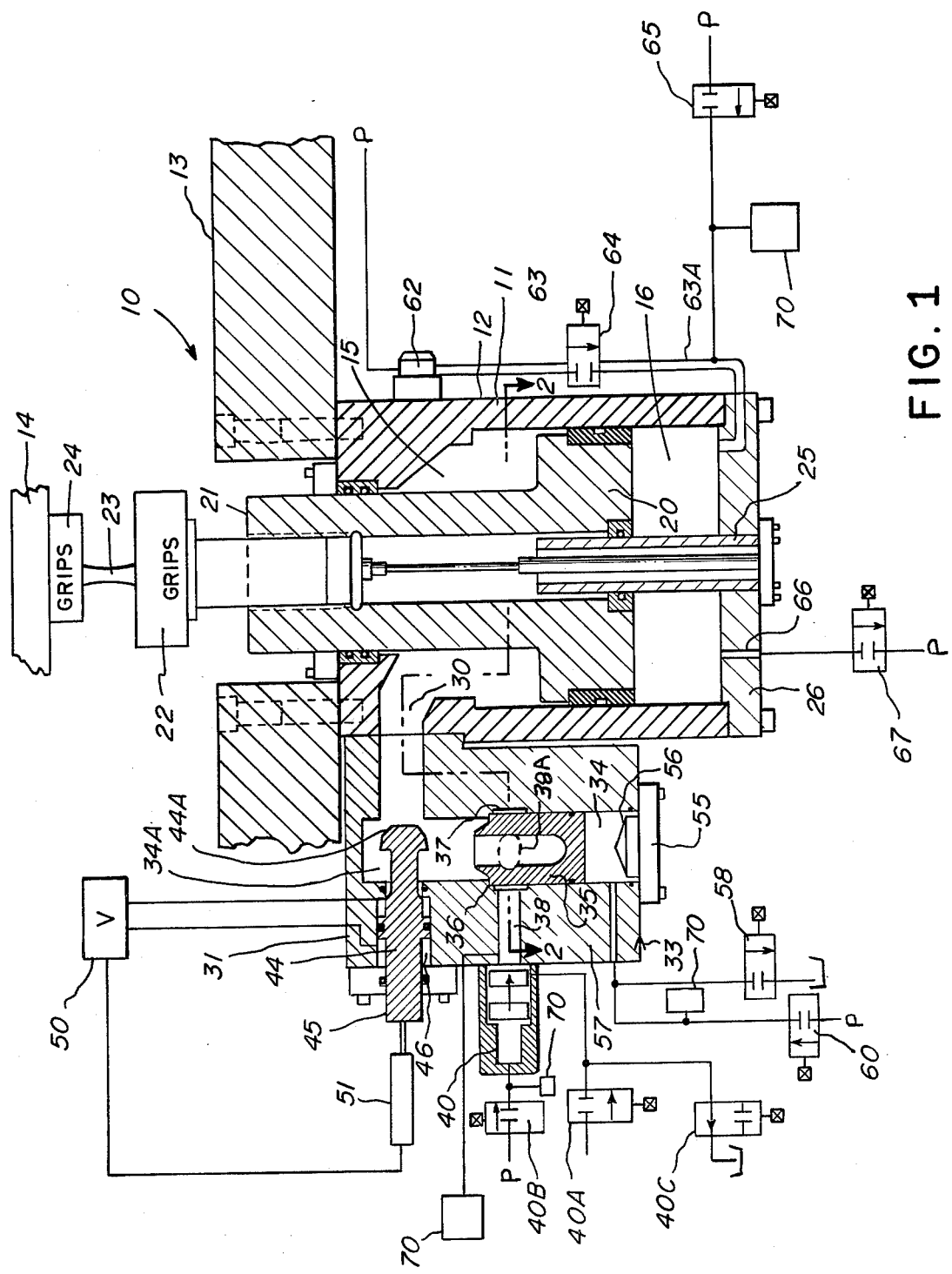
FIG. 1 is a vertical sectional view of an actuator and high rate valve made according to the present invention, with parts schematically shown.
Figure 2:
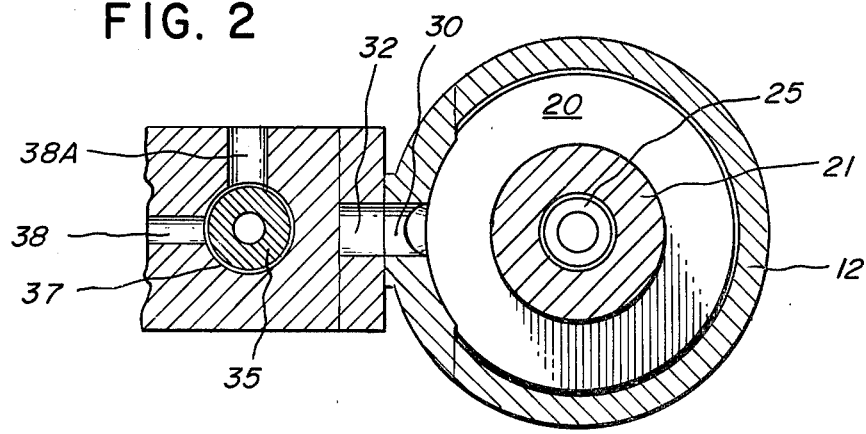
FIG. 2 is a sectional view taken generally along line 2—2 in FIG. 1.

FIG. 1 shows a cross sectional view of a typical actuator assembly illustrated generally at 10 which is used with a high rate valve of the present invention. The actuator 11 as shown is a fluid pressure actuator having an outer cylinder housing 12, which is mounted suitably to a base plate 13 of a load frame assembly which includes an upper crosshead support 14. The portions 13 and 14 are shown only fragmentarily, but they do comprise portions of a standard load frame used for testing specimens and the load applied is supported by crosshead 14. The actuator housing or cylinder 12 has a first interior chamber 15 and a second interior chamber 16 formed on opposite sides of a piston 20 which reciprocates within the cylinder or housing 12, and the piston has an integral rod 21 which extends through a seal at one end of the housing 12. The rod 21 in turn is connected mechanically in a suitable manner to lower specimen grips 22. The lower specimen grips 22 hold one end of a test specimen 23, the other end of which is held in upper grips 24 that are mounted to the upper crosshead 14 of the load frame.

The specimen 23 to be tested as shown is tested in tension, and will usually be loaded under high rates of load to failure. A load transducer may also be used to measure the load on the specimen. A stroke and velocity transducer indicated generally at 25 is connected between a base plate 26 of the actuator assembly and the piston rod 21, to provide a signal indicating the position of the piston and rod during its operation. The piston carries suitable seals to seal the piston with respect to the wall of the chambers in which it operates in the normal manner.

The housing or cylinder 12 has a port 30 which passes through one wall of the cylinder, and a high rate valve assembly 31 is connected to have the valve outlet passageway 32 opening to this port. Suitable sealing means are provided to seal the junction between the cylinder and the valve assembly.

It should also be noted that the cylinder or housing 12 is suitably connected to the load frame base plate 13 with suitable cap screws, and under tension loading of the specimen will be bearing against the base plate.

The valve assembly 31 includes a valve housing 33 which has an internal bore indicated 34. A valve piston member or poppet 35 is slidably mounted in this bore. The piston slides in the bore 34, and will seat against an annular shoulder 36 defined in the bore 34. It should be noted that the upper portion of the bore indicated at 34A is of slightly smaller diameter than the portion in which the valve piston 35 is mounted. The valve piston 35 includes an annular sealing surface that seats against the shoulder 36. The bore 34 is open to an annular recess 37 which is on an opposite side of shoulder 36 from the bore portion 34A, and this recess 37, forms an inlet open through suitable passageway 38 to a fluid pressure accumulator or other source of fluid under pressure indicated generally at 40. The accumulator 40 can be of any desired construction, and is of sufficient volume so that it will provide adequate flow through the passageway 38, and additional passageways that may be provided, such as a passageway shown in dotted lines at 38A, to provide the necessary velocity of actuation. The preferred accumulator is a piston type that provides a known quantity of hydraulic oil to operate the actuator.

The bore portion 34A opens to passageway 32 and an adjustable throttle valve indicated generally at 44 is mounted to control the size of the opening between the passageway portion 34A and the passageway 32. The throttle valve 44 has a valve head 44A which is adapted to seat on the edge of and close the circular cross section passageway 32. The valve 44 has a shank carrying a piston 46 mounted in a bore 47 and the valve is slidable linearly along its central axis 45 to a desired position spaced from the port formed by the passageway 32 where it joins the bore portion 34A. Cylinder bore 47 is formed in the valve body 33, and the position of the throttle valve 44 can be controlled by controlling the amount of fluid under pressure on opposite sides of the piston 46.

The bore 47 is thus connected to a suitable valve 50 to adjust the amount of hydraulic oil on opposite sides of piston 46 and which valve can be controlled in response to a signal or signals from a stroke transducer 51 that is attached to the valve 44 to determine the position of the valve head 44A, and thus the opening size between the bore portion 34A and the passageway 32.

On the opposite side of the main valve piston 35 from the shoulder 36 there is a chamber formed in the bore 34, which in this instance forms a control chamber 34B. The valve piston 35 thus effectively divides the chamber 34 into two sections 34A and 34B. The outer end of the chamber or bore 34 is closed with a cap 55 which also carries a bumper 56 which acts as a cushion for the valve piston 35 when the valve is opened. The control chamber 34B is open through a passageway 57 to a trigger valve 58, and also to a normally closed valve 60 which leads to a source of gaseous fluid under pressure such as nitrogen to provide a pressure charge in the control chamber 34B. The pressure in control chamber 34B holds the valve piston 35 against the shoulder 36. The normally closed valve 60 is opened to charge the control chamber 34B and closed after the control chamber is pressurized. As will be explained, the firing or operation of the valve and the test actuator is accomplished by opening the valve 58 (which is also normally closed) to dump this fluid under pressure in the control chamber 34B and reduce the pressure in the control chamber.

The accumulator 40 also may have suitable charge connection, and valves 40A and 40B permit it to be charged with hydraulic oil on the side open to passageway 38 and with a gaseous fluid on the control side. The external valves used are usually solenoid operated valves with the solenoids represented by small boxes adjacent the valves.

The chamber 16 of the actuator assembly 11 is also filled with a suitable gas under pressure at a desired pressure level. The actuator is made so that it can be operated with hydraulic fluid in a normal manner through the use of a servovalve 62 which is connected to suitable ports leading to the chamber 15. The servovalve is also connected through a conduit 63 to the chamber 16, and this conduit has a shut off valve (normally closed) indicated at 64 which is closed when the unit is operating in a high rate test configuration. The portion of the conduit 63A leading to the chamber 16 from the valve 64 is connected through a suitable control valve 65 to a source of gaseous fluid under pressure, and the chamber 16 also is connected through a drain passageway 66 to a normally closed valve 67 leading to a drain. When the actuator is to be used in high rate configuration, the valve 64 is left closed, and after any hydraulic oil in chamber 16 is removed, valve 65 is opened to precharge the chamber 16 in a desired level with gaseous fluid under pressure. The valve 65 is permitted to close again. Valve 67 remains closed.

If the actuator is to be used in the normal servovalve control mode, the valve 67 would be opened to dump the nitrogen or other gaseous fluid under pressure from the chamber 16, and valve 64 would be opened to permit the servovalve to control the actuator.

OPERATION

Assuming that the throttle valve 44 is positioned in its desired location to control the velocity at a desired level, and that the specimen 23 is attached to the grips in the desired manner, the high rate valve is initiated by triggering dump valve 58 to dump the fluid under pressure (which in this form is a gaseous fluid) from the control chamber 34B. The hydraulic fluid under pressure from accumulator 40 acting in the passageway 38 and through the recess 37 also acts to tend to escape past the seat where the valve piston 35 seats against the shoulder 36. Once the control chamber pressure is reduced the oil from accumulator 40 will start to push the piston 35 back toward the bumper 56. As soon as the valve piston 35 cracks open a small amount the pressure from the accumulator 40 (and also a second accumulator 40 acting through passageway 38A shown in dotted lines) will be acting on the valve piston head and will slam the valve piston 35 open almost instantaneously. The valve piston 35 will go from just barely cracking open to full open in an extremely short time, for example one millisecond. All of the fluid under pressure from the accumulator is rapidly dumped and flows through the bore portion 34A, passageway 32, and port or passageway 30 into the chamber 15 to act against the piston 20 and at a very high rate slam the piston 20 toward the base plate 26 of the actuator. The specimen 23, of course will be loaded in tension at the rate controlled by the throttle valve 44 and will reach its break load at the desired rate. The gaseous fluid in chamber 16 acts as a cushion for piston 20 and is not sufficiently high to adversely effect the rate of the loading on the specimen.

In this form of control, the servovalve 62 can be opened to dump the fluid under pressure from the chamber 15 to drain to reposition the lower grips, and a new specimen can be placed into position. The accumulator 40 (and a second accumulator as well) would be recharged with oil on its base side open to the passageway 38, and with the gaseous fluid on the opposite side of the accumulator member in the normal manner. The high rate valve piston of course would be moved to its closed position by charging chamber 34B through the valve 60 prior to recharging the accumulator 40. A valve 40C also can be used for bleeding the oil side of the accumulator 40 if desired, and the gaseous fluid on the accumulator 40 also can be bled off if desired.

Various pressure transducers which are indicated only schematically at 70 are provided in the lines to provide means for controlling the desired pressures in various chambers. It should be noted also that the pressure transducer 70, which is utilized for sensing the pressure in chamber 16 (in the line leading from valve 65) can be used as a safety override to prevent firing of the high rate valve piston, unless there is pressure in the chamber 16 sufficient to provide a cushion.

It also is quite apparent that compression testing can be carried out by providing a rod on the opposite side of the piston 20 leading out to the base plate 26 of the actuator.

The rod 21 of the actuator assembly can be positioned with the servovalve 62 or other external valves if desired in order to get the specimen grips in place holding the test specimen, and manual valves could also be used as well as programmed solenoid valves for operating the high rate valve piston 35. The high speed tensile tests are used primarily for testing the strain rate sensitivity of metals or plastics.

The valve piston 35 is thus a fast acting piston member which is held closed by controls which may be triggered. Once the piston starts to open, it will open almost instantaneously by having only a small effective area subjected to action of the main supply pressure until the valve cracks open and thereafter subjecting a substantial cross section area to the supply pressure for opening action. The ports leading from the pressure source comprising accumulator 40 to the close coupled actuator may be selected to be very large and the control valve port is fully opened immediately. The throttle valve 44 is utilized for determining the velocity of operation by controlling the flow of fluid under pressure or hydraulic fluid into the actuator chamber 15.

Figure 3:
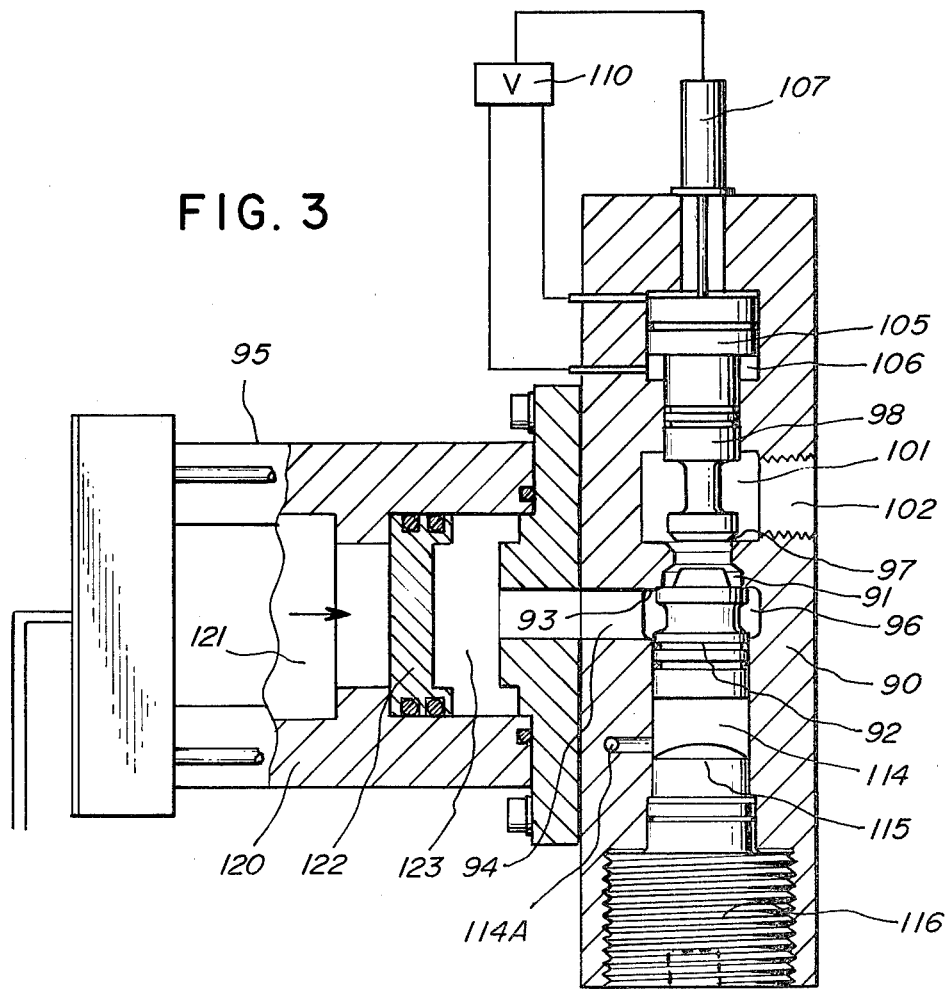
FIG. 3 is a sectional view of a preferred form of the control valve of the present invention.

A preferred embodiment of the high rate fast opening valve is shown in FIG. 3, and it includes a valve block 90 which has an interior bore 91 in which a valve piston member 92 is mounted. The valve piston member in this form seats against a shoulder 93 formed in the valve body. A passageway 94 leads from the output of an accumulator assembly 95 to an annular recess 96 surrounding the valving end of valve piston 92. It can be seen that the bore 91 also has an interior ring or shoulder forming a valve seat 97 against which a throttling valve 98 will seat. The valve seat 97 controls flow from bore 91 to a chamber 101 that in turn is open to a passageway 102 corresponding to the passageway 32 of the previous form of the invention. The passageway 102 thus is connected directly to the actuator to be used.

The throttling valve 98 is a spool which has a piston member 105 integral therewith, or attached thereto. The piston 105 operates in chamber 106 for actuation. A stroke transducer 107 is connected to the piston 105, and the position of the piston 105 is controlled through a valve 110 equivalent to the valve 50. Note that the ports of valve 110 are open to chamber 106 on opposite sides of the piston 105 so that the axial movement of the throttle valve 98 toward and away from seat 97 can be controlled to control the opening across valve seat 97.

The valve piston member 92 is seated in a bore portion 114, which forms a control chamber into which suitable gaseous fluid under pressure can be introduced to tend to urge valve piston 92 to seat on shoulder 93 and to be thus held in closed position, much as previously described in relation to the chamber 34B. When the valve is to be fired, the pressure in the control chamber 114 is bled off, and pressure from the accumulator 95 acting to open valve piston 99 will overcome the pressure in the chamber 114 urging the valve piston 92 back toward a stop block 115 which is mounted in a threaded plug 116 in the body 90. The stop block 115 is an elastomeric member which will cushion the movement of the valve piston 92 as it is driven open.

The accumulator 94 has an accumulator body 120, and is provided with an interior gas side chamber 121 that is charged with a suitable pressure from a source of gaseous fluid under pressure and which is connected to the output of a valve such as valve 40B in FIG. 1, and this pressure acts against a piston 122 that is sealably mounted in a second portion of the interior chamber of the body 120. The piston 122 therefore forms a chamber 123 that is open to the passageway 94. Chamber 123 is filled with hydraulic oil, which will act on the valve body 92, and when the fluid pressure in chamber 114 is bled out through the passageway indicated at 114A as controlled by a valve corresponding to the valve 58 in the first form of the invention, the hydraulic oil pressure will open the piston and move it away from the shoulder 93. The tendency is for the oil to flow out around the seal formed at shoulder 93. Note that "O" rings are used for seals on piston 92 and there is a tendency for the pressure from accumulator 120 to push the valve piston 92 open. As soon as the valve piston cracks open a little, the entire end portion of the piston 92 will be exposed to the pressure from chamber 123 and passageway 94, and the valve piston will be driven open against the stop 115, thereby opening the port leading to the annular recess 96 fully, and almost instantaneously. There are usually two such accumulators 120 open to the annular recess 96, as previously explained. The hydraulic oil will be forced out past the valve seat 97 at a rate controlled by the position of the throttle valve 98, and out through the passageway 102 to the controlled actuator. The quantity of hydraulic fluid that is in the chamber 123 is controlled to a known amount, and thus the amount of flow out the passageway 102 whenever the valve body 92 is fired or opened will be a known quantity to also control the amount of movement of the actuator that is being controlled.

By regulating the valve 110, the position of throttle valve 98 can be controlled so that the opening in the cross valve 97 is controlled to provide means for controlling the velocity of operation.

The principle of operation of the form of the invention shown in FIG. 3 is exactly the same as that shown partially schematically in FIG. 1, and shows a working embodiment as well as the details of the preferred form of accumulator.

It should also be noted that in certain instances the specimen grip may provide a certain amount of slack before test actuation so that when the high rate valve is fired the piston 20 will accelerate as it takes up slack prior to the time that load is applied to the specimen so that when the specimen is loaded the piston 20 and rod 21 are already moving at a high rate of speed. In other instances, the specimen can be gripped with no slack for tension loading and thus loaded across the entire leading cycle of the actuator.

The selection of passageway and port sizes, and the accumulator size for the main pressurizing accumulator can be calculated to achieve the speed of actuation if desired. The actuator is capable of achieving full velocity in 0.003 to 0.005 seconds, and in a very short travel, for example in the range of one tenth of an inch. Strokes of the rod 21 can range to three or more inches, however.

It should also be noted that once the pressure in the control chambers 34B or 114 is reduced sufficiently to achieve a force balance on the valve piston which permits the valve piston to crack open, the piston will be driven open and the remaining gaseous fluid in the control chamber will merely be compressed. It does not all have to escape.

Because of the difference in effective areas acted upon when the valve piston is closed, the control chamber pressure may be much lower than the main supply pressure.

What is claimed is:

1. In a specimen testing system, an actuator utilized for compression or tension testing of a specimen at a controllable velocity and for a controlled distance along a linear axis, an actuator cylinder having an internal piston and a control rod connected to said specimen, the improvement comprising a high rate fast opening valve to control incompressible fluid under pressure to act on said cylinder including a valve body, accumulator means comprising a chamber having an output connection and being formed in part by a movable piston defining an output chamber portion having a known amount of incompressible fluid therein, pressurized gas means urging said movable piston to provide the known quantity of incompressible fluid at the output connection of the accumulator means, a bore in said valve body having an inlet port and an outlet port, passageway means connecting the output connection of the accumulator means to the inlet port, said actuator being fluidly coupled to said outlet port, a poppet valve piston mounted in said bore and movable from a closed position wherein it closes off flow from said inlet port to said outlet port to an open position where said poppet valve piston permits flow from said inlet port to said outlet port, said poppet valve piston having portions open to said substantially incompressible fluid under pressure at said inlet port when the poppet valve piston is in closed position, and being urged thereby toward open position, menas to provide a second compressible fluid under pressure on said poppet valve piston urging said poppet valve piston to position closing off flow from said inlet port to said outlet port, means to permit selectively reducing the second fluid under pressure to a level which permits the poppet valve piston to start to move to open position, substantial surface portions of said poppet valve piston thereafter being acted on by the first fluid to move the poppet valve piston to open position at a substantially increased force and to fully open the poppet valve piston and discharge the output chamber portion of the accumulator means and to provide only the known quantity of the incompressible fluid to the actuator to load said attached specimen rapidly for a controlled amount of movement, and an adjustable throttle valve means positioned in the fluid flow path between said poppet valve piston and said outlet port to adjustably control the size of the flow path for the known quantity of incompressible fluid under pressure.

2. The combination as specified in claim 1 and cushion means to arrest and stop the movement of said poppet valve piston when it reaches its open position.

3. The improvement of claim 1 further characterized by said actuator internal piston dividing the cylinder into first and second chamber portions, a first chamber portion having an actuator port opening to said outlet port, and means to provide a compressible fluid communicating with said second chamber portion to provide a cushion for movement of said internal piston tending to reduce the volume of said second chamber portion.

4. The combination of claim 3 wherein said valve body is mounted directly on said actuator and the outlet port and actuator inlet port mate directly with each other.

5. The combination of claim 4 wherein said means to provide a compressible fluid communicating with said second chamber comprises means to fill said second chamber portion with a gaseous fluid.

* * * * *